United States Patent [19]

Kojima et al.

[11] Patent Number: 4,533,639

[45] Date of Patent: Aug. 6, 1985

[54] TEST METHOD FOR PHOSPHATE COATINGS

[75] Inventors: Ryuji Kojima; Akiko Yazaki, both of Tokyo, Japan

[73] Assignee: Parker Chemical Company, Madison Heights, Mich.

[21] Appl. No.: 622,431

[22] Filed: Jun. 20, 1984

[30] Foreign Application Priority Data

Jun. 21, 1983 [JP] Japan ................................ 58-110254

[51] Int. Cl.³ .......................... G01N 1/00; G01N 33/20
[52] U.S. Cl. ............................................ 436/2; 436/5; 436/81; 436/84; 436/103; 436/175
[58] Field of Search .................. 436/2, 5, 81, 84, 103, 436/175, 177

[56] References Cited

U.S. PATENT DOCUMENTS

| | | | |
|---|---|---|---|
| 3,615,825 | 10/1971 | Gansser | 134/2 X |
| 3,671,447 | 6/1972 | Kowalski | 134/2 X |

FOREIGN PATENT DOCUMENTS

| | | | |
|---|---|---|---|
| 1623322 | 12/1970 | Fed. Rep. of Germany | 436/2 |
| 49-6740 | 2/1974 | Japan | 134/2 |

*Primary Examiner*—Arnold Turk
*Attorney, Agent, or Firm*—Arthur E. Kluegel

[57] ABSTRACT

A method for determining the coating weight and composition of a zinc phosphate coating on a ferrous metal surface comprises stripping the coating from a known area using an aqueous solution of sodium hydroxide and triethanolamine, thereafter measuring the iron and phosphate contents by colorimetric analysis of the stripping solution and then determining the coating weight and composition based on such measurements.

4 Claims, No Drawings

TEST METHOD FOR PHOSPHATE COATINGS

BACKGROUND OF THE INVENTION

This invention concerns a test method for phosphate coatings on iron based surfaces.

Conventionally phosphate coatings have been widely used industrially as an undercoating for paint in order to improve the adhesion of the paint and to improve corrosion resistance. It is known that the weight of the phosphate coating and the proportions of hopeite ($Zn_3(PO_4)_2.4H_2O$) and phosphophillite ($Zn_2Fe(PO_4)_2.4H_2O$) in the coatings (this ratio is referred to below as P/P+H) have an effect on the adhesion of the paint and on the corrosion resistance, and these are important characteristics which determine the efficiency of a phosphate coating.

Conventional methods for determining the weight of a coating are shown in Table 1.

TABLE 1

| Method of Measurement | Type of Test | Measuring Time | Sample Area | Equipment | Sample Sectioned |
|---|---|---|---|---|---|
| x-ray fluorescence | non-destructive | 20 seconds | 1–5 cm$^2$ | x-ray fluorescence analyzer | Yes |
| Stripping with aqueous chromic acid | Destructive | 30 minutes | 50–200 cm$^2$ | Direct indicating balance | Yes |

It is clear from Table 1 that determination of the weight by means of X-ray fluorescence has the advantage of permitting measurements to be made in a short period of time, but the equipment is expensive for a production line and there is a disadvantage in that the sample has to be sectioned. Furthermore, the method of stripping with aqueous chromic acid has been used conventionally for determining the weight of a coating but the stripping is carried out at a high temperature and takes a long time and there is a further disadvantage in that a chemical treatment must be carried out with the waste because of the presence of hexavalent chromium.

The conventional method for determining the value of P/P+H for a phosphate coating involves the use of X-ray diffraction. However, measurements cannot be made with this method while the object is at a high temperature after being phosphate treated and the equipment is expensive and it is not practical for a production line. There are other methods besides X-ray diffraction analysis in which the zinc ion and iron ion concentrations in an aqueous solution obtained by stripping with aqueous chromic acid are determined but this has the same disadvantages as the aforementioned method for determining the weight of the coating using an aqueous chromic acid stripping liquor. Furthermore, the zinc ion and iron ion concentrations cannot be determined colorimetrically because of the high chromic acid content. The analysis is normally carried out using atomic absorption spectroscopy, but the equipment is expensive and this is not practical as a production line method. Furthermore, if the P/P+H value obtained by X-ray diffraction is taken to be 100%, then the result obtained with the stripping method is quite low at 84% and this is undesirable.

The aim of this invention is to provide a test method for phosphate coatings which is free from these disadvantages.

SUMMARY OF THE INVENTION

The test method for phosphate coatings which achieves the aim of this invention is a method in which the distinguishing features are that the phosphate coating on an iron based metal surface is stripped off and dissolved with an aqueous solution which contains sodium hydroxide and triethanolamine and that the weight of the phosphate coating and the composition of the phosphate coating are determined.

DETAILED DESCRIPTION OF THE INVENTION

The concentration of the sodium hydroxide is preferably 2~25%, the concentration of the triethanolamine is preferably 0.5~10% and, for the sake of simplicity, the temperature when stripping and dissolving the phosphate coating with the aqueous solution which contains these materials is preferably normal temperature.

The invention is described below by means of examples.

EXAMPLE 1

Two phosphate treated steel plates were immersed at normal temperature (20° C.) for 5 minutes in an aqueous solution which contained 50 g/l of sodium hydroxide and 10 ml/l of triethanolamine and the weights of coating were determined. The results were similar to those obtained with the conventional stripping method with chromic acid (5% aqueous solution of anhydrous chromic acid, 72°–78° C.) as is shown in Table 2.

TABLE 2

| Stripping Method | Example 1 | | Reference Example (Chromic acid stripping method) | |
|---|---|---|---|---|
| n | 1 | 2 | 1 | 2 |
| Weight before stripping | 57.5868 g | 56.1261 g | 56.9742 g | 57.5479 g |
| Weight after stripping | 57.5036 g | 56.0419 g | 56.8589 g | 57.4691 g |
| Weight difference | 0.0836 g | 0.0797 g | 0.0853 g | 0.0788 g |
| Area stripped | 180 cm$^2$ | 180 cm$^2$ | 180 cm$^2$ | 180 cm$^2$ |
| Weight of Coating | 4.55 g/m$^2$ | 4.47 g/m$^2$ | 4.71 g/m$^2$ | 4.31 g/m$^2$ |
| Average Value | 4.51 g/m$^2$ | | 4.51 g/m$^2$ | |

EXAMPLE 2

A kit for testing phosphate coatings.
(1) Equipment and Apparatus Used
 (a) Spectrophotometer (Spectronic Mini 20, made by Bosch and Lomb)
 (b) Resin embedding ring (internal diameter 2.5 cm, Height 2.5 cm, made of plastic.)
 (c) Measuring flasks (50 ml, 200 ml, 1 liter).
 (d) Dropper pipette.
 (e) Beaker and other normal apparatus.
(2) Reagents.
 (a) Coating stripping liquor NaOH (100 g) is dissolved in distilled water, 20 ml of triethanolamine is added and the whole is made up to 1 liter.
 (b) "Bracoat SM-5" (Made by Sekisui Kagaku, adhesive)
 (c) Standard $PO_4^{3-}$ ion solution (0.1 mg $PO_4^{3-}$/ml).
 (d) Standard $Fe^{2+}$ ion solution (0.1 mg $Fe^{2+}$/ml).

(e) Ammonium molybdate solution. Ammonium molybdate tetrahydrate (15 g) is dissolved in about 150 ml of water, 182 ml of concentrated sulfuric acid is added and the whole is made up to 1 liter.
(f) Tin (II) chloride solution. Tin (II) chloride dihydrate (1 g) is dissolved in 5 ml of hydrochloric acid and made up to 50 ml with water and a small piece of tin is added. (Stored in a colored bottle).
(g) Ascorbic acid.
(h) o'-phenanthroline solution. o'phenanthroline monohydride (1 g) is dissolved in 100 ml of 95% ethanol and made up to 1 liter with water.
(i) 50% ammonium acetate solution.
(j) Phenolphthalein indicator solution.
(k) 50 w/w% sulfuric acid.

The aforementioned equipment of section (1) and the reagents of section (2) may be packed in a portable case as a single unit.

TEST METHOD FOR PHOSPHATE COATINGS (1) Method for Stripping Off the Coating
(a) The bottom 2 or 3 mm of the embedding ring are soaked with the "Bracoat", the excess "Bracoat" is removed and the ring is pressed out in the treated surface and left to dry. This ring serves to expose only a predetermined area of the test surface to stripping.
(b) The coating stripping liquor (5 ml) is poured into the ring.
(c) After 1 minute precisely has elapsed the stripping liquor is sucked up and transferred to the 50 ml measuring flask using the dropper pipette. The ring is then washed twice with water, the washings are added to the same measuring flask and then the flask is made up to the mark with water.
(d) The ring is removed from the treated plate and the stripped area is calculated. (outside diameter/2)-×(inside diameter/2)×$\pi$.

(2) Colorimetric Method for Fe
(a) The coating stripping liquor solution (25 ml) from (1) above is transferred in a 50 ml measuring flask.
(b) One drop of phenolphthalein indicator is added and then the contents are titrated with 50 w/w% sulfuric acid until the color changes from pink to colorless.
(c) About 0.2 g of ascorbic acid is added, any material which has adhered to the walls is washed down with water, the ascorbic acid is dissolved and the whole is then left to stand for about 5 minutes.
(d) o'-phenanthroline solution (5 ml) is added and then 5 ml of 50% ammonium acetate solution is added and the volume is made up to the mark with water.
(e) The absorbance at 510 nm is measured after about 20 minutes and the Fe content is calculated from a calibration curve prepared beforehand.
(f) The procedure is repeated using water as a blank. Fe ($\mu$g) in the stripped area = Fe ($\mu$g) obtained from calibration curve × 50 ml/25 ml (3) Colorimetric Method for PO$_4$
(a) The coating stripping liquor solution (10 ml) from (1) above is transferred in a 50 ml measuring flask.
(b) One drop of phenolphthalein indicator is added and then the contents are titrated with 50 w/w% sulfuric acid until the color changes from pink to colorless.
(c) Ammonium molybdate solution (5 ml) is added and, after shaking, about 0.25 ml of tin (II) chloride solution is added and the flask is filled up to the mark with water and shaken.
(d) The absorbance at 700 nm is measured after about 15 minutes and the PO$_4{}^{3-}$ content is calculated from a calibration curve which has been prepared beforehand.
(e) The procedure is repeated using water as a blank. PO$_4$ ($\mu$g) in the stripped area = PO$_4$ ($\mu$g) obtained from the calibration curve × 50 ml/10 ml (4) Calculation of the Coating Weight The coating weight is obtained from the PO$_4$ content obtained via the PO$_4$ colorimetric method of (3) above. PO$_4$ ($\mu$g) in the stripped area = PO$_4$ ($\mu$g) obtained from the calibration curve × 50/10

$$\text{Weight of PO}_4 \text{ per unit area (g/m}^2) = \text{PO}_4 (\mu g) \text{ in stripped area} \times \frac{10^4}{\text{Stripped area}} \times 10^{-6}$$

Weight of coating (g/cm$^2$) = Weight of PO$_4$ per unit area (g/m$^2$) × 2.38675.

(5) Calculation of P/P+H for the coating. The weight ratio of Fe ($\mu$g) and PO$_4$($\mu$g) (=Fe/PO$_4$) is calculated for the stripped area and P/P+H is obtained using the formula below.

$$y = -0.13457x^2 \times 100 + 8.116x - 0.25119$$

x: Fe/PO$_4$ y = P/P+H (6) Results of Tests on Phosphate Coatings The results of test carried out with phosphate treated steel plates are shown in Table 3.

TABLE 3

| | Reference Examples | | Examples | | | | |
|---|---|---|---|---|---|---|---|
| Sample | P/P + H by x-ray diffraction | Weight of Coating by Chromic Acid Method | Area Stripped (cm$^2$) | Analytical Values in Stripped Area | | P/P + H Calculated From Fe/PO$_4$ | Coating Calculated From PO$_4$ (g/m$^2$) |
| | | | | Fe ($\mu$g) | PO$_4$ ($\mu$g) | Fe/PO$_4$ | | |
| 1 | 0.87 | 1.03 | 4.333 | 40 | 160 | 0.25 | 0.99 | 0.88 |
| 2 | 0.79 | 2.02 | 4.427 | 79 | 397.5 | 0.199 | 0.83 | 2.14 |
| 3 | 0.25 | 3.08 | 4.333 | 37.5 | 520 | 0.072 | 0.24 | 2.86 |
| 4 | 0.29 | 4.11 | 4.427 | 53.5 | 680 | 0.079 | 0.29 | 3.67 |
| 5 | 0.26 | 4.89 | 4.427 | 62.5 | 790 | 0.079 | 0.29 | 4.26 |
| 6 | 0.41 | 2.89 | 4.333 | 40 | 480 | 0.083 | 0.32 | 2.64 |
| 7 | 0.41 | 2.89 | 4.522 | 48 | 505 | 0.095 | 0.39 | 2.67 |
| 8 | 0.35 | 3.79 | 4.153 | 51.5 | 635 | 0.081 | 0.31 | 3.65 |
| 9 | 0.35 | 3.79 | 4.333 | 55 | 677.5 | 0.081 | 0.31 | 3.73 |

As shown above, by means of this invention, it is possible to determine the weight of the phosphate coating and the composition of the phosphate coating on an iron based metal surface both cheaply and easily.

What is claimed is:

1. A method for determining the coating weight and composition of a zinc phosphate coating on a ferrous metal surface, comprising:
    (a) stripping the coating for a known period from a known area of the surface using a solution comprising sodium hydroxide and triethanolamine;
    (b) colorimetrically determining the iron content of the stripping solution;
    (c) colorimetrically determining the phosphate content of the stripping solution;
    (d) determining the weight ratio of hopeite/phosphophillite; and
    (e) determining the coating weight.

2. The method of claim 1 wherein the stripping solution contains from 2-25 wt. % sodium hydroxide and from 0.5 to 20 wt.% triethanolamine.

3. The method of claim 1 wherein the iron is determined colorimetrically by titration to the phenophthalein end point with sulfuric acid followed by addition of ascorbic acid, o'-phenanthroline and ammonium acetate and the absorbance at 510 nm vs. standard is determined.

4. The method of claim 1 wherein the phosphate is determined colorimetrically by titrating to the phenolphthalein end point using sulfuric acid followed by addition of ammonium molybdate and tin (II) chloride and the absorbance at 700 nm vs. standard is determined.

* * * * *